United States Patent [19]
Saffer et al.

[11] Patent Number: 5,838,764
[45] Date of Patent: Nov. 17, 1998

[54] MEDICAL SYSTEM WITH ADJUSTABLE HANDLE

[75] Inventors: Edmund Saffer, Eggolsheim; Helmut Richter, Baiersdorf; Hans-Juergen Schweiger, Erlangen, all of Germany

[73] Assignee: Siemens Aktiengesellschaft, Munich, Germany

[21] Appl. No.: 881,915

[22] Filed: Jun. 25, 1997

[30] Foreign Application Priority Data

Jun. 25, 1996 [DE] Germany ............... 196 25 411.6

[51] Int. Cl.⁶ ..................................................... G05G 5/00
[52] U.S. Cl. ........................................... 378/197; 378/205
[58] Field of Search ................................. 378/193, 167, 378/170, 189, 197, 198, 204, 205; 200/57 R, 52 R

[56] References Cited

U.S. PATENT DOCUMENTS 4,095,071  6/1978  Chamberlain ........................... 200/157
4,993,057  2/1991  Runnells ................................. 378/197
5,165,786  11/1992  Hubert ..................................... 362/287

FOREIGN PATENT DOCUMENTS

G 84 18 335   7/1985   Germany .
G 88 12 768  10/1988   Germany .
OS 41 08 593  9/1992   Germany .
G 94 11 387  10/1994   Germany .

*Primary Examiner*—David P. Porta
*Attorney, Agent, or Firm*—Hill & Simpson

[57] ABSTRACT

A medical system with adjustable, movable components that can be set by disengageable brakes, in particular an X-ray diagnostic apparatus with a C-arm that can be adjusted in the height of its orbital position and angulation and that carries an X-ray source and a beam receiver at its ends, has a sterilizeable handle that can be plugged in various positions, with a plug lock. A disengage button for the system brakes is arranged on the handle, which can be engaged with switching apparatuses in the system upon plugging the handle into a component of the system. The button can then be operated for actuating and disengaging the brakes.

17 Claims, 4 Drawing Sheets

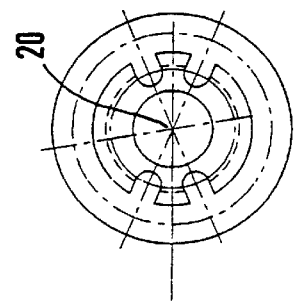
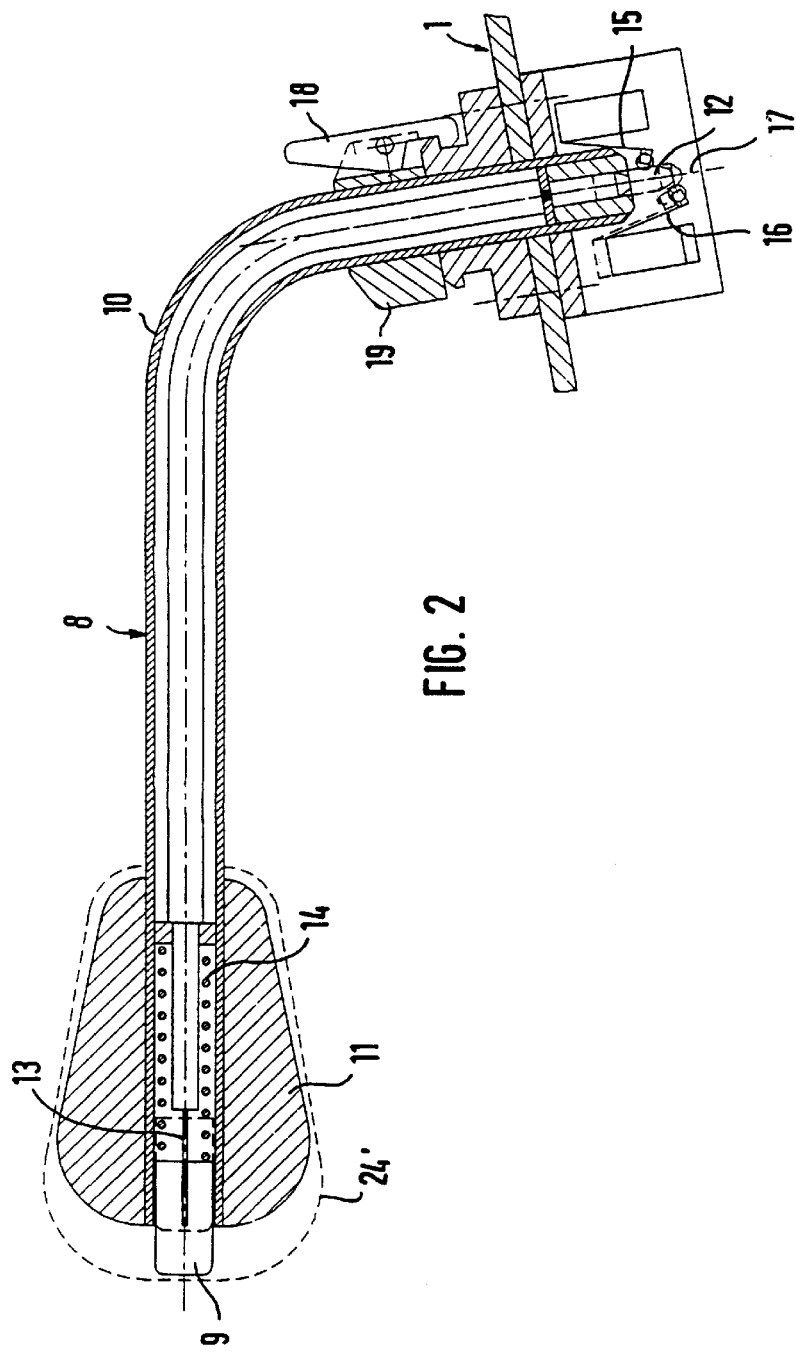

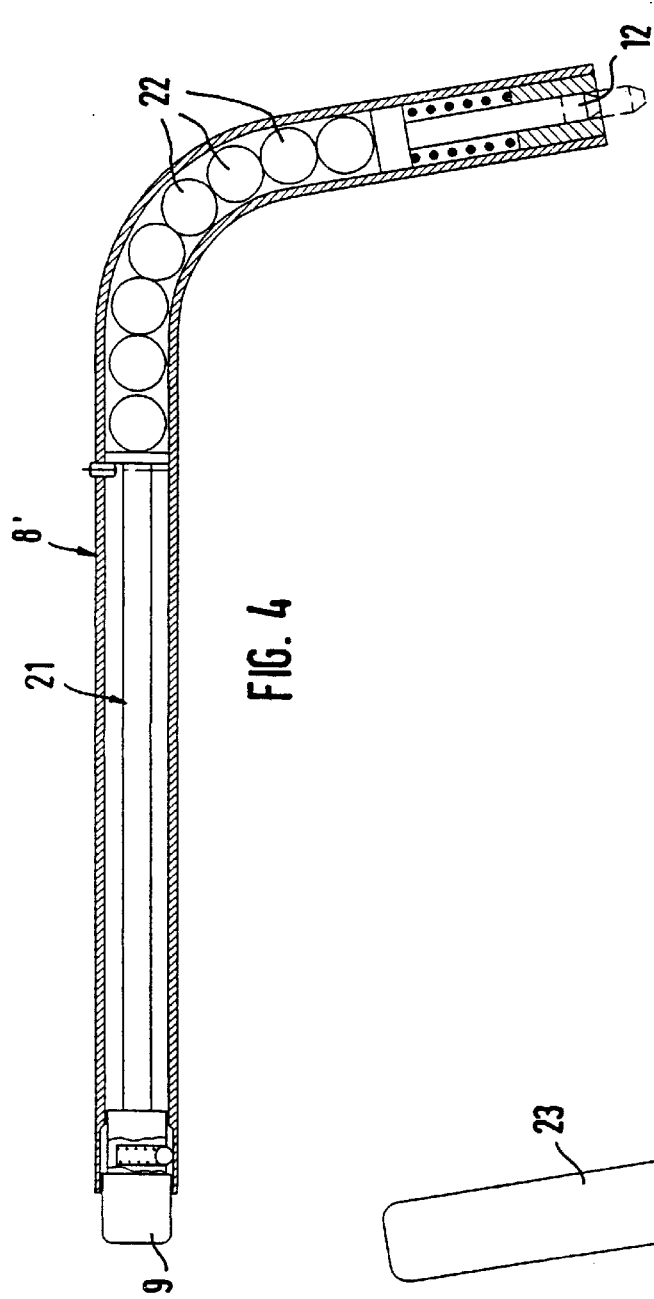
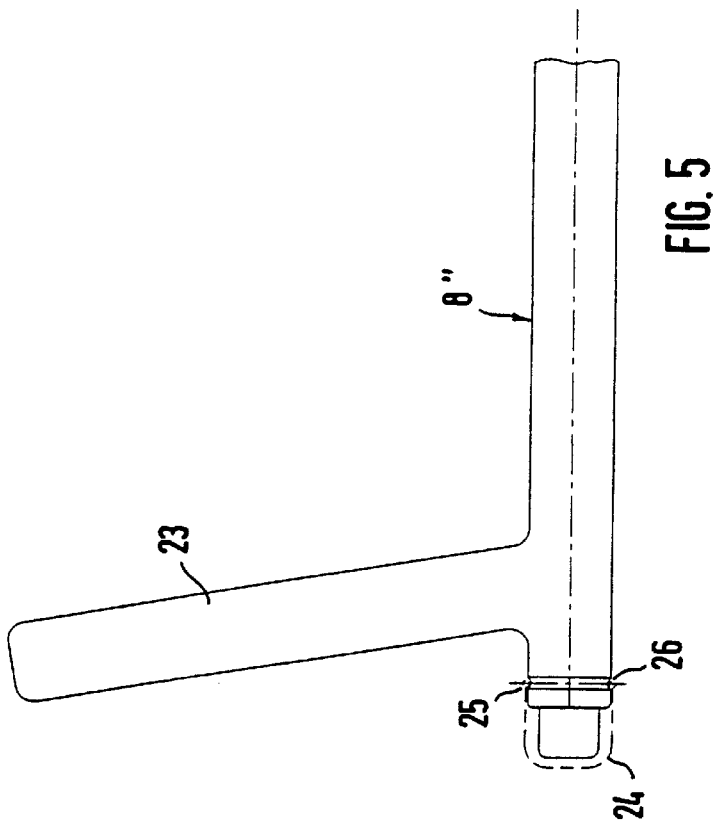

FIG. 6A
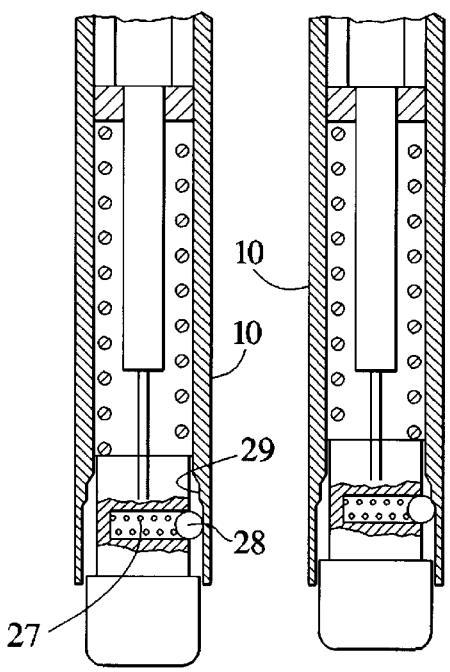
FIG. 6b
FIG. 6c
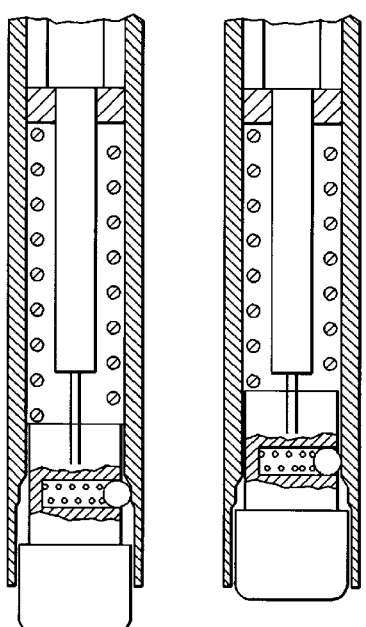
FIG. 6d
FIG. 7A
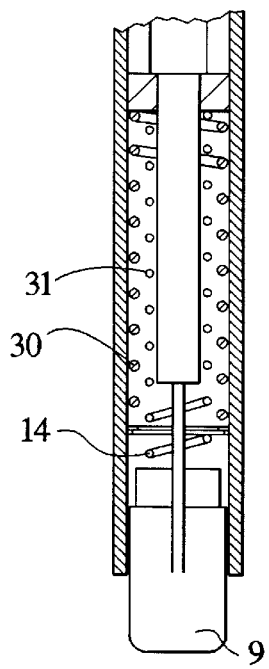
FIG. 7B
FIG. 7C
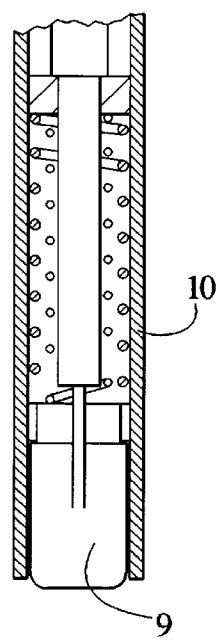

MEDICAL SYSTEM WITH ADJUSTABLE HANDLE

BACKGROUND OF THE INVENTION

1. Field of the Invention

The present invention is directed to a medical system of the type having adjustable components (movable) that are each held in place, once adjusted in position, by means of disengageable brakes, in particular an X-ray diagnostic apparatus with a C-arm that can be adjusted as to the height of its orbital position and angular plane and that carries a source of X-rays and a beam receiver at its respective ends, with a sterilizeable handle that can be plugged in various positions, with a plug lock at the grip. The handle is used by an attendant to move (adjust) the C-arm to a selected position when its brake is disengaged.

2. Description of the Prior Art

An arrangement of the above general type as described, for example, in German OS 41 08 593, enables a person to set up the apparatus by gripping the sterile handle so that the operator can carry out the orientation of the X-ray source and the beam receiver. This arrangement, however, in which the handle can be set in various positions within the same receptacle, or can be plugged in different receptacles in the apparatus, enables only the manual adjustment of the individual movable components. A second operator is still required to disengage and reset the brakes required for the setting of the components in the desired position, since the controls for brake disengagement are remote from the handle location.

In German Utility Model 88 12 768, in order to avoid this disadvantage of requiring a second person for the disengagement and re-engagement of the brakes, it was proposed to form the braking apparatus as an electromechanical brake whose braking effect is produced by the force of a spring and which can be disengaged by means of an electromechanical element, with the operating switches being disposed for example directly on the X-ray source in a manner so as to be sterilizeable. Although this allows the operator to disengage and set the brakes without loss of the sterilization, it presents the difficulty that there is no sterile point of contact for adjusting the apparatus.

SUMMARY OF THE INVENTION

An object of the present invention is to provide a medical system of the type initially described which allows a way that a person, under sterile conditions, to actuate and disengage the brakes, and also to set up the apparatus using a sterile handle.

The above object is achieved in a medical system of the type initially described having a disengagement control element for the system brakes arranged on the handle, with the control element being connected to a switching arrangement in the system upon being plugged into the handle receptacle, by means of connections in the handle.

Preferably the handle is plugged in the C-arm.

Although it is possible to provide electrical plug connections, via which a pushbutton arranged on the sterile handle and likewise sterilizeable can be connected with the system brakes, in the construction of the invention preferably actuation elements are arranged in each of the plug-in recesses for plugging the handle to the respective adjustable components (for simplicity, in the following a C-arm of an X-ray diagnostic apparatus will always be discussed as the adjustable component). The actuation elements can be actuated by a switching pin that extends of the plugged-in end of the handle upon depression of a pushbutton at the opposite (free) end.

For this purpose, the handle can preferably have a curved tube in which a Bowden cable connects a switching button at one end with the switching pin at the other end; with the switching button and the switching pin each being biased into their respective extended positions by springs.

As an alternative to this Bowden cable embodiment, which can cause problems for sterilization due to the lubrication generally provided for smooth operation thereof, the tube can contain a rod, which is moved within the tube when the switching button is depressed, followed by a series of balls in the region of the bend, in order to connect the switching button with the switching pin.

In order to be able to actuate several brakes independently of one another in a very simple way using only one switching button, in a further embodiment of the invention several actuation elements offset in the plugging direction, are provided, and the switching pin has several different projection positions. Depending on how far the switching button has been pressed and how far out the switching pin has been caused to project as a result, one or more of the actuation elements is actuated. Each actuation element has a lever which projects into the path of displacement of the switching pin in order to actuate the associated brakes.

In order to allow the operator to distinguish among and achieve the individual switching points, the switching button can be depressed either against a switching resistance that causes a graduated or stepped increase of the pressure force required to depress the button at the different functional settings. This can ensue in a very simple manner by providing pressure springs in order to increase the pressure force in the various pressure settings of the switching button (corresponding to the various projection positions of the switching pin). Alternatively a spring-loaded locking ball can be provided, that is pushed against inner shoulders of the tube that project inwardly to different extents. This distinction in the switching (depressing) force can then clearly ensue both at the switching button and at the switching pin.

Since the differentiation of the individual actuation elements ensues only by virtue of the projection length of the switching pin, the actuation elements can be arranged radially around the switching pin so as to be angularly offset relative to one another, which simplifies the housing and also makes it possible for the switching distances, i.e. the axial offsets, to be kept very small.

It is particularly advantageous that the actuation elements can disengage or set not only respective different brakes, but also entire groups of brakes in common, in order to enable, with one actuation, the actuation and resetting of, if necessary, two or more brakes simultaneously, for the most important basic adjustments.

For simpler maintenance of sterilization, the switching button can either be covered by a disposable cap, such as a silicone cap, which can for example be plugged over the switching button and which is releaseably stopped at an edge shoulder on the handle. Alternatively, a sterilizeable covering, in particular a plastic covering, can also be provided to cover the switching button.

All parts of the handle should be fashioned either from stainless metal and/or from plastics that can withstand thermal stress up to at least 140° C., so that the entire handle can be sterilized as a whole in an autoclave.

It is also within the scope of the invention to position a stopping hook on the plug-in end of the handle, which can be snapped into counter-snaps on the system. This stop button, which is actuated for replugging of the handle, is likewise sterilizeable due to its arrangement on the handle, so that it can be operated in the same way by the operator as the switching button for the brakes.

DESCRIPTION OF THE DRAWINGS

FIG. 2 shows a section through a first embodiment of an inventive handle, as well as the counter-plugging parts on the C-arm.

FIG. 3 shows a surface view of the plug receptacle without the handle.

FIG. 4 shows a view of a second embodiment of the handle with a rod-ball connection between the pushbutton and the switching pin.

FIG. 5 shows a fragmentary side view of the end at the actuation side of a modified inventive handle with an L-shaped construction.

FIGS. 6a to 6d show longitudinal sections, through the end at the switching button, of an inventive handle, with a graduated increase of the switching resistance in the different switching positions.

FIG. 7a to 7c show sections, corresponding to FIGS. 6a to 6d, through a further embodiment of an inventive handle, in which the switching button is displaced against connectable springs.

DESCRIPTION OF THE PREFERRED EMBODIMENTS

Figure 1:
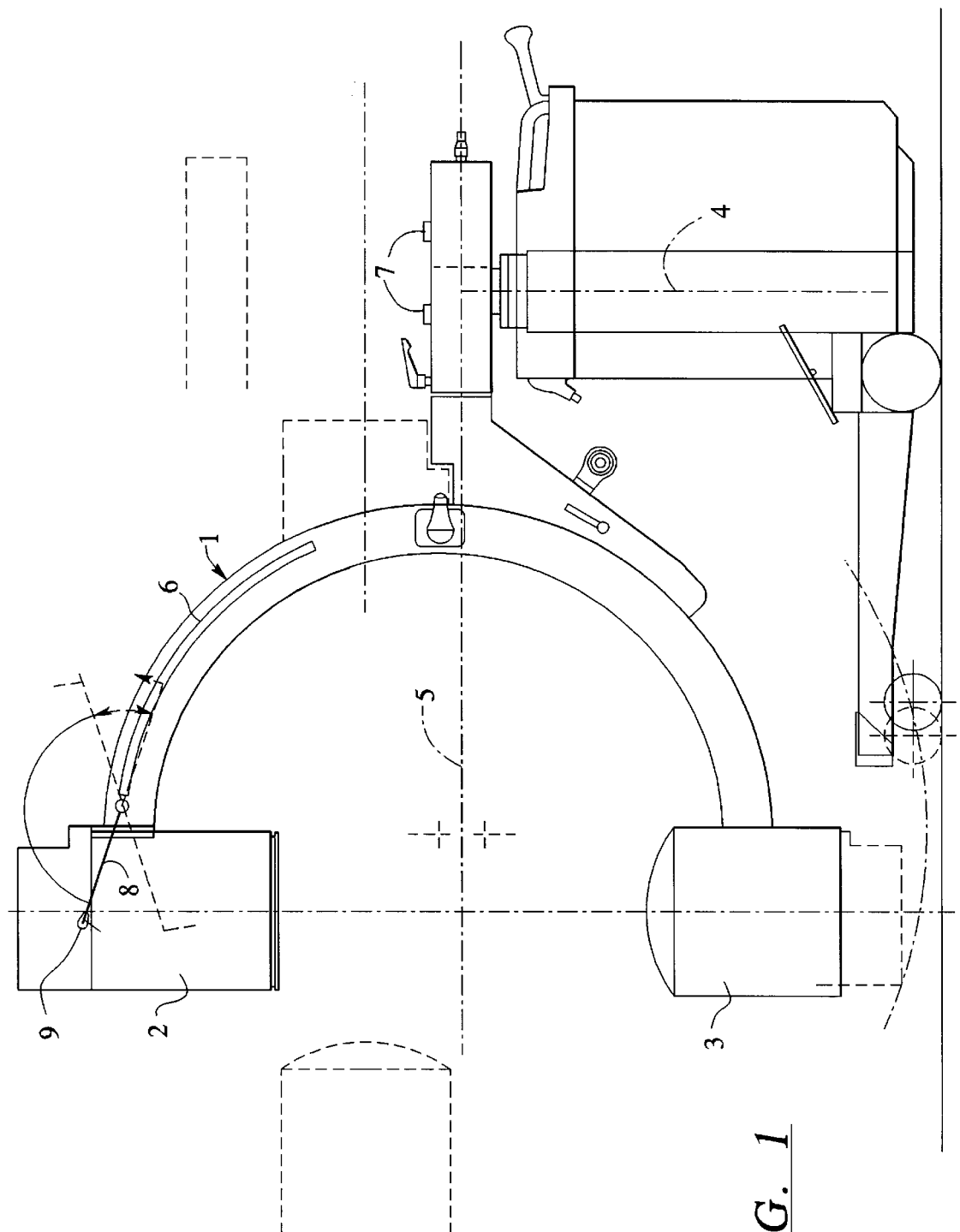
FIG. 1 is a schematic illustration of an inventive X-ray diagnostic apparatus with an adjustable C-arm and a sterile handle that can be plugged onto the C-arm.

In the X-ray diagnostic apparatus shown schematically in FIG. 1, an adjustable C-arm 1 supports an X-ray source 3 and a beam receiver 2 at its opposite ends. This C-arm can be adjusted in height in the direction of the axis 4, and can also be rotated around the axis 5, and an angular displacement is also possible in the direction 6 of the C-curve. All these degrees of freedom are blocked by disengageable braking apparatuses. These brakes can, for example, be released by disengage keys 7 and can be engaged again after the desired setting has ensued. For manipulation, i.e. in order to carry out the adjustment motions, a sterilizeable handle 8 that can be releaseably plugged onto the C-arm 1 is provided. The handle 8 at its free end has a switching button 9 that can be better seen in detail in the following drawings, by means of which the various brakes can be disengaged and reset individually or in groups. In this way, i.e. by means of the provision of a sterilizeable handle with a corresponding pushbutton (also sterilizeable), the operator can adjust the X-ray apparatus by himself or by herself under sterile conditions during the operation, without requiring a second operator. The handle 8 can not only be plugged in four different angular positions, as shown in FIG. 1, but also further plugging positions, arranged in offset fashion, can be provided on the apparatus for attachment of the handle 8.

FIG. 2 shows a first embodiment of an inventive sterilizeable handle. This sterilizeable handle 8 has a bent tube 10 with the aforementioned switching button 9 at its free end (at 11, a thickening of the grip for the purpose of easing handling can be seen), as well as a switching pin 12 positioned at the other end. In the embodiment according to FIG. 2 the switching pin 12 is connected with the switching button 9 via a Bowden cable 13. The switching button 9 with the Bowden cable 13 is biased outwardly into a rest position by means of a spring assembly 14, while the switching pin 12 is biased into its projecting position by means of another spring assembly (not shown). If the switching button 9 is pressed against the spring 14, the spring (not shown) of the switching pin 12 pulls this pin outwardly by the amount of the pressing in of the switching button 9, so that it can actuate the actuation elements 15 and 16 arranged in the plug opening on the apparatus. These calipers 15, 16, whose levers protrude into the path of motion of the switching pin 12, are arranged in angularly distributed fashion around the switching peg, and are also spaced apart in the direction of its projection axis 17, so that, depending on how far the switching pin 12 has projected, first the adjustment element 15, and then the adjustment element 16, and, if necessary, additional axially displaced adjustment elements are actuated. The angular displacement around the projection axis 17 thereby has two advantages. On the one hand, the adjustment elements can be housed very simply, and on the other hand—and this is of particular importance—the axial displacement of two switches in relation to one another can be kept relatively small, so that, accordingly, the switching path, i.e. the extent of the depression of the switching button 9, can be kept small. A locking hook 18 is carried at the plug-in end of the handle 8 and is engageable with a selected one of a number of recesses in a collar 19 which surrounds the receptacle 20. This allows the handle 8 to be plugged into different positions on the C-arm 1. FIG. 3 shows a surface view of the C-arm 1, without the handle 8. The handle 8 can be plugged and stopped in various angular positions around the receptacle 20.

The inventive handle 8 according to FIG. 2 can easily be sterilized as a whole, due to the construction of all the parts from stainless metal and/or sterilizeable plastics (i.e. plastics that withstand higher temperatures), but it is possible that problems may arise concerning the smooth running of the Bowden cable 13. To avoid this, in the embodiment shown in FIG. 4 of a modified handle 8', the switching button 9 and the switching pin 12 are connected with one another by means of a rod 21 with a series of balls 22 in the turning area. A rod embodiment of this sort does not require a Bowden cable, which has to run smoothly and thus requires frequent lubrication; the rod solution is thus easier to sterilize.

The embodiment of an inventive handle according to FIG. 5 is distinguished from that according to FIGS. 2 and 4 chiefly by the additional L-shaped angled grip 23. In addition, in the handle 8" in FIG. 5 a silicone cap 24 fashioned as a disposable component is provided, whose annular bead 25 projects into a groove 26 of the tube 10 in order to prevent soiling of the switching button 9. In FIG. 2, a sterilizeable plastic covering 24' is provided for the same purpose.

In order to be able to distinguish among the various switching points for the actuation of the various actuation elements 15 and 16, two generally distinguishable solutions are possible, shown in FIGS. 6 and 7. In FIG. 6, a locking ball 28 that is radially outwardly biased in the switching button 9 by a spring 27 is provided, which lies against the stepped inner wall 29 of the tube 10. When a transition takes place from one switching position to the other, there ensues a stepped jump of the inner wall 29, which manifests itself as a switch resistance that increases abruptly, so that the operator recognizes that a further switching stage has been passed, and that the next actuation element was thereby actuated. In the exemplary embodiment shown, three such switching stages are available, and the actuation of three different actuation element is correspondingly possible.

In the embodiment according to FIG. 7, various connectable springs 30 and 31 are provided, so that when the different depression positions are reached for the actuation of different actuation elements, a step-by-step increase in the pressure force results, which is again noticeable by the operator, so that it is recognized that a further actuation element has now been actuated. The actuation elements 15 and 16 (of course, the number can also be greater than two) can thereby serve not only for the actuation of individual brakes, but also entire groups of brakes. With three actuation elements, the actuation may, for example, be as follows:

1. all brakes set 2. actuation element 1: brake horizontal stroke and pivoting disengaged 3. actuation element 2: brake angulation and vertical stroke and orbital stroke disengaged 4. actuation element 3: brake horizontal stroke and pivoting set.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical system comprising:

a plurality of movable components each having a disengageable brake for holding that component, after adjustment thereof, in an adjusted position, at least one of said components having a plug-in receptacle;

each brake having switching means associated therewith for engaging and disengaging that brake;

a sterilizeable handle having a gripping end and an opposite plug-in end releaseably receivable in said plug-in receptacle; and means contained in said handle, including a manually depressable pushbutton at said gripping end of said handle, for operating at least one of said switching means when said plug-in end of said handle is received in said plug-in receptacle.

2. A medical system as claimed in claim 1 wherein said medical system comprises an X-ray source and a beam receiver and a C-arm having opposite ends at which said X-ray source and said beam receiver are respectively attached, said C-arm comprising said at least one of said components having said plug-in receptacle.

3. A medical system as claimed in claim 1 wherein said plug-in receptacle comprises means for receiving said plug-in end of said handle at a plurality of different angular positions.

4. A medical system as claimed in claim 1 wherein said means for operating said switching means comprises a switching pin which is caused by depression of said pushbutton to project beyond said plug-in end of said handle, and wherein each switching means comprises an actuation element disposed in said receptacle for engagement with said switching pin.

5. A medical system as claimed in claim 1 comprising a plurality of actuation elements, respectively connected to different switching means, disposed spaced from each other along a projection direction of said switching pin, and wherein said means for operating comprises means, dependent on depression of said pushbutton, for extending said switching pin through a plurality of different extended positions for respectively engaging said plurality of actuation elements.

6. A medical system as claimed in claim 5 wherein said means for operating comprises means for producing increasing switching resistance against depression of said pushbutton as said pushbutton is depressed.

7. A medical system as claimed in claim 5 wherein said means for operating comprises means for producing switching resistance increased in steps against depression of said pushbutton as said pushbutton is depressed.

8. A medical system as claimed in claim 6 wherein said means for operating comprises a plurality of concentrically disposed springs in said handle which successively act on said pushbutton as said pushbutton is depressed.

9. A medical system as claimed in claim 6 wherein said means for operating comprises a spring-biased locking ball carried at a side of said pushbutton, and wherein said handle has an interior bore into which said pushbutton is depressed having a plurality of shoulders of respectively different diameters which successively engage said ball as said pushbutton is depressed.

10. A medical system as claimed in claim 5 wherein said plurality of actuation elements are respectively angularly offset relative to each other around said switching pin.

11. A medical system as claimed in claim 5 wherein at least one actuation element is associated with more than one of said switching means.

12. A medical system as claimed in claim 1 wherein said handle comprises a curved tube, and wherein said means for operating comprises a Bowden cable connecting said pushbutton and said switching pin, and bias means for biasing each of said pushbutton and said switching pin out of said curved tube.

13. A medical system as claimed in claim 1 wherein said handle comprises a curved tube and wherein said operating means comprises a rod and a series of balls contained in said tube mechanically connecting said pushbutton and said switching pin, said balls being disposed in a curved region of said tube.

14. A medical system as claimed in claim 1 further comprising a silicone cap covering said pushbutton.

15. A medical system as claimed in claim 1 further comprising a sterilizeable plastic cover covering said pushbutton.

16. A medical system as claimed in claim 1 wherein said handle consists entirely of materials capable of withstanding thermal loading of at least 140° C.

17. A medical system as claimed in claim 1 wherein said handle comprises a locking hook and wherein said receptacle comprises at least one element for engaging said locking hook, said locking hook being temporarily engageable in said engagement element when said plug-in end of said handle is received in said receptacle, for holding said handle in said receptacle.

* * * * *